United States Patent [19]

Takada et al.

[11] Patent Number: 5,320,917
[45] Date of Patent: Jun. 14, 1994

[54] FLUORIDE IONIC CONDUCTOR

[75] Inventors: Kazunori Takada; Shigeo Kondo, Osaka, both of Japan

[73] Assignee: Matsushita Electric Industrial Co., Ltd., Osaka, Japan

[21] Appl. No.: 815,009

[22] Filed: Dec. 27, 1991

[30] Foreign Application Priority Data

Jan. 14, 1991 [JP] Japan ..................... 3-2636

[51] Int. Cl.$^5$ ........................... H01M 10/36
[52] U.S. Cl. ................... 429/191; 429/199; 423/464
[58] Field of Search ............ 429/191, 199; 423/464

[56] References Cited

U.S. PATENT DOCUMENTS

| | | | |
|---|---|---|---|
| 3,266,867 | 8/1966 | Muhler | 423/464 |
| 3,594,116 | 7/1971 | Donaldson | 423/464 |
| 4,707,224 | 11/1987 | Shabrang | 429/191 X |
| 4,851,303 | 7/1989 | Madou et al. | 429/191 X |

OTHER PUBLICATIONS

Communication form the European Pat. Off. dated Jul. 22, 1992.
P. Darbon et al., "Conductivite Anionique Des Phases Appartenant Au Systeme PB52 —ZRF4," *Materials Research Bulletin*, 16, pp. 389-395 (1981), Oxford, GB.
P. Darbon et al., "Evolution Des Properties De Transport Des Solutions Solides . . . ," *Solid State Ionics, 2,* pp. 131-138 (1981), Amsterdam, The Netherlands.
P. Lagassie, "Etude Comparative Des Proprietes Electriques Des Solutions Solides PBI-xSNxF2 . . . ," *Solid State Ionics, 21,* pp.343-348 (Nov. 1986), Amsterdam, The Netherlands.
J. M. Reau et al., "Diffusion and Short-Range Order in PB1-xINxF2+x . . . ," *Solid State Ionics, 31,* pp. 147-157 (Nov. 1988), Amsterdam, The Netherlands.
J. Lucas, "Fluoride Solid Electrolytes," *Chemical Abstracts, 95,* Abstract No. 122787U, p. 493, col. 2 (1981), Columbus, Ohio.
J. P. Laval, "Synthesis and Characterization of the Solid Phase of the System Zirconium Fluoride (ZrF4)-Barium Fluoride (BaF4)," *Chemical Abstracts 92,* p. 699, col. 1 (1980), Columbus, Ohio.
J. P. Laval, "Une Nouvelle Structure Ordonnee Derivee De La Fluorine (Pb3ZrF10)," *Materials Research Bulletin, 14,* pp. 1517-1524 (1979), Oxford, GB.
Y. Kawamoto, "Fluorine Nuclear Magnetic Resonance and Fluoride Ion conduction in Vitreous and Crystalline Barium Fluorozirconates," *Physics and Chemistry of Glasses, 31,* No. 3, pp. 117-121 (1990) Sheffield, GB.

*Primary Examiner*—Stephen Kalafut
*Attorney, Agent, or Firm*—Panitch, Schwarze, Jacobs & Nadel

[57] ABSTRACT

The present invention provides an ionic conductor used for a solid electrolyte with a high ionic conductivity including fluorine, an element belonging to the fourth group or the second group of the periodic table and zirconium. The invention also provides an ionic conductor including fluorine, lead or tin and zirconium. The invention also provides an ionic conductor being $Pb_{1-x}Sn_{1-y}Zr_{x+y}F_{4+2x+2y}$ wherein $0<x+y\leq 0.16$. The invention further provides an ionic conductor being $Pb_{1-x}Sn_{1-y}Zr_{x+y}F_{4+2x+2y}$ wherein $0<x+y\leq 0.02$.

5 Claims, 3 Drawing Sheets

FLUORIDE IONIC CONDUCTOR

BACKGROUND OF THE INVENTION

1. Field of the Invention

The present invention relates to a solid electrolyte used for a cell, a sensor such as an ionic sensor and an electrochemical display element and the like and more particularly to an ionic conductor in which fluoride ions conduct.

2. Description of the Prior Art

A fluoride ionic conductor such as $\beta$-$PbF_2$, $CaF_2$, $LaF_3$, and the like have been generally known. The electrolytic conductivity (the ionic conductivity) of these materials is about $10^{-6}$ S/cm at room temperature. Recently Reau et al. have found that $PbSnF_4$ has a high ionic conductivity of $10^{-3}$ S/cm.

A cell, an ionic sensor and the like are suggested as elements using these fluoride ionic conductors.

In an ionic conductor of a solid electrolyte, an excellent ionic conductivity at room temperature is particularly desirable, because when an electrochemical element such as a cell, a sensor, an electrochemical display element and the like is made of the solid electrolyte, the ionic conductivity is related with the inside impedance of the element: The excellent ionic conductivity of the solid electrolyte makes the inside impedance of the electrochemical element formed thereby low. On the contrary, poor ionic conductivity makes the inside impedance high, resulting in deteriorating discharge efficiency in a cell, and slowing speed of response in a sensor and an electrochemical display element. Therefore, the ionic conductivity of the solid electrolyte needs to be improved at room temperature.

The present invention provides a fluoride ionic conductor with improved ionic conductivity.

SUMMARY OF THE INVENTION

The ionic conductor used for a solid electrolyte of this invention, which overcomes the above-discussed and numerous other disadvantages and deficiencies of the prior art, comprises fluorine, an element of the fourth group of the periodic table and zirconium.

In a preferred embodiment, the element of the fourth group of the periodic table is lead or tin.

In a preferred embodiment, the ionic conductor is $Pb_{1-x}Sn_{1-y}Zr_{x+y}F_{4+2x+2y}$ wherein $0 < x+y \leq 0.16$.

In a preferred embodiment, the ionic conductor is $Pb_{1-x}Sn_{1-y}Zr_{x+y}F_{4+2x+2y}$ wherein $0 < x+y \leq 0.02$.

In a preferred embodiment, the ionic conductor has a fluorite crystal structure.

In a preferred embodiment, the fluorine is in the form of an anion, and the zirconium and the element are in the form of a cation.

Alternately, an ionic conductor used for a solid electrolyte comprises fluorine, zirconium and an element, which belongs to the second group in the periodic table.

In a preferred embodiment, the ionic conductor has a fluorite crystal structure.

In a preferred embodiment, the fluorine is in the form of an anion, and the zirconium and the element are in the form of a cation.

Thus, the invention described herein makes possible the objectives of providing (1) a fluoride ionic conductor used for a solid electrolyte with a high conductivity, (2) an ionic conductor used for a solid electrolyte comprising fluorine, zirconium and an element of the fourth group of the periodic table, (3) an ionic conductor used for a solid electrolyte comprising fluorine, lead and tin, (4) an ionic conductor used for a solid electrolyte with a composition of $Pb_{1-x}Sn_{1-y}Zr_{x+y}F_{4+2x+2y}$ (wherein $0 < x+y \leq 0.16$) and (5) an ionic conductor used for a solid electrolyte comprising fluorine, zirconium and an element of the second group of the periodic table.

BRIEF DESCRIPTION OF THE DRAWINGS

This invention may be better understood and its numerous objects and advantages will become apparent to those skilled in the art by reference to the accompanying drawings as follows.

DESCRIPTION OF THE PREFERRED EMBODIMENTS

Example 1

The first example of the present invention will now be described in detail.

A fluoride ionic conductor with a composition of $Pb_{1-x}Sn_{1-x}Zr_{2x}F_{4+4x}$ (wherein $0 < x \leq 0.08$), which is the composition of $Pb_{1-x}Sn_{1-y}Zr_{x+y}F_{4+2x+2y}$ (wherein $0 < x+y \leq 0.16$) when $x = y$, is obtained as follows:

Lead fluoride ($PbF_2$), tin fluoride ($SnF_2$) and zirconium fluoride ($ZrF_4$) are used to prepare a sample. $PbF_2$, $SnF_2$ and $ZrF_4$ are weighed so as to make the molar ratio $1-x:1-x:2x$, then crushed and mixed with an agate mortar (the average particle diameter: 50 $\mu$m). The crushed powder is pelletized with a diameter of 10 mm, a thickness of 3 mm and a powder density of 4.7 g/cm$^3$ by a compression molding machine (temperature: room temperature, pressing time: 10 sec.).

The pellet is put in a reaction tube of nickel, the air in which has been exchanged for argon. Then hydrogen fluoride and argon as carrier gas are made to flow through the tube at a flow rate of 20 ml/min., and the tube is heated at 350° C. for six hours, thereby obtaining a sintered sample.

As a comparative example, a fluoride ionic conductor with a composition of $PbSnF_4$ is obtained. The same procedure as above is repeated to obtain a sintered sample except for using $PbF_2$ and $SnF_2$ with a 1:1 molar ratio.

In the thus obtained sintered sample of the fluoride ionic conductor gold is deposited as electrodes by vacuum evaporation. The electric conductivity of the sample is measured in argon by the AC impedance measuring method (temperature: 20° C. to 300° C.).

Figure 1:
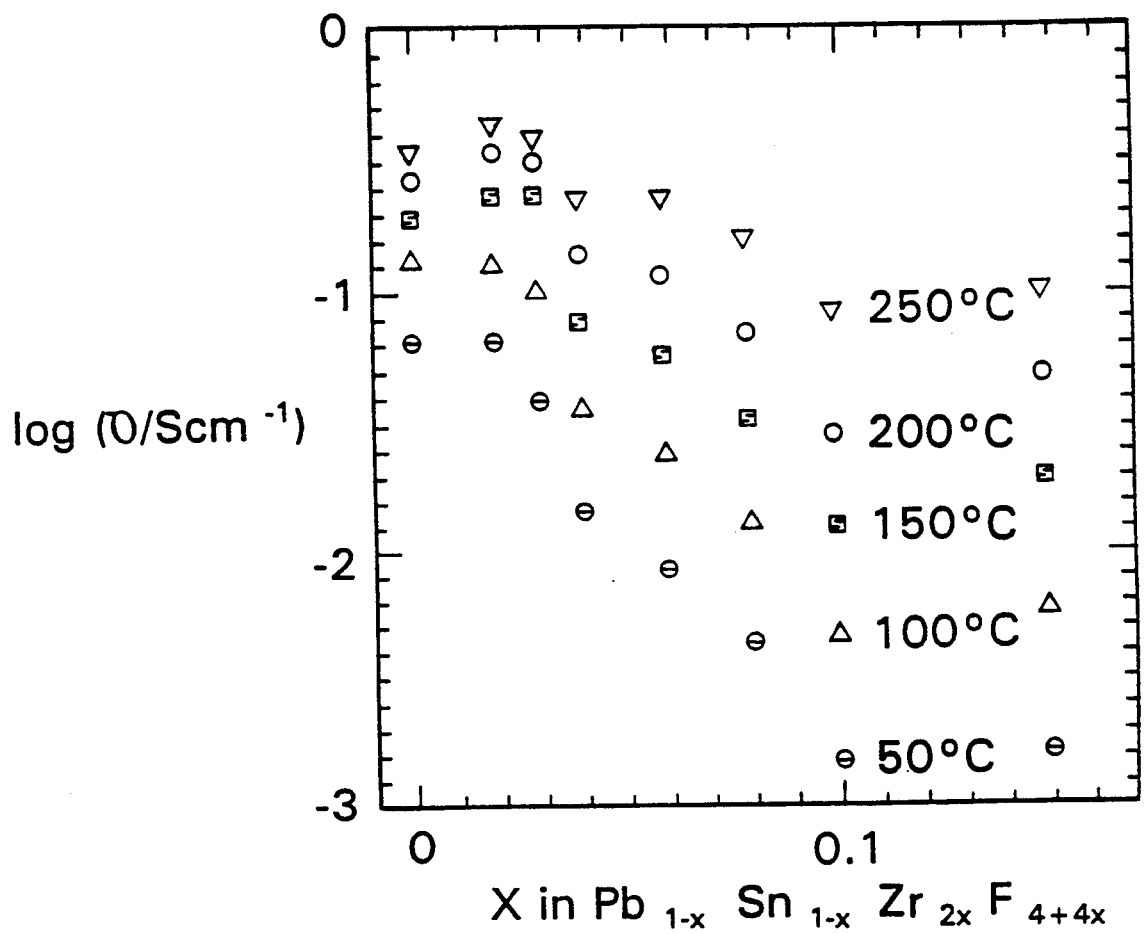
FIG. 1 is a diagram showing the relationship between the zirconium ion concentration of the fluoride ionic conductor and the electric conductivity according to the first example of the present invention.

As shown in FIG. 1, the relationship between the zirconium ion concentration (x) and the electric conductivity at each temperature is as follows:

$x = 0.000$, at a temperature of 60° C. with an electric conductivity of $3.2 \times 10^{-2}$ S/cm $x = 0.005$, at a temperature of 60° C. with an electric conductivity of $7.6 \times 10^{-2}$ S/cm $x = 0.010$, at a temperature of 60° C. with an electric conductivity of $9.1 \times 10^{-2}$ S/cm $x = 0.020$, at a temperature of 60° C. with an electric conductivity of $3.0 \times 10^{-2}$ S/cm $x = 0.030$, at a temperature of 60° C. with an electric conductivity of $8.1 \times 10^{-3}$ S/cm $x = 0.040$, at a temperature of 60° C. with an electric conductivity of $4.3 \times 10^{-3}$ S/cm $x = 0.050$, at a temperature of 60° C. with an electric conductivity of $1.5 \times 10^{-3}$ S/cm $x = 0.000$, at a temperature of 100° C. with an electric conductivity of $8.7 \times 10^{-2}$ S/cm $x = 0.005$, at a temperature of 100° C. with an electric conductivity of $1.3 \times 10^{-1}$ S/cm $x = 0.010$, at a temperature of 100° C. with an electric conductivity of $1.9 \times 10^{-1}$ S/cm $x = 0.020$, at a temperature of 100° C. with an electric conductivity of $8.7 \times 10^{-2}$ S/cm $x = 0.030$, at a temperature of 100° C. with an electric conductivity of $2.8 \times 10^{-2}$ S/cm $x = 0.040$, at a temperature of 100° C. with an electric conductivity of $1.3 \times 10^{-2}$ S/cm $x = 0.050$, at a temperature of 100° C. with an electric conductivity of $4.8 \times 10^{-3}$ S/cm $x = 0.000$, at a temperature of 150° C. with an electric conductivity of $1.6 \times 10^{-1}$ S/cm $x = 0.005$, at a temperature of 150° C. with an electric conductivity of $2.3 \times 10^{-1}$ S/cm.

$x = 0.010$, at a temperature of 150° C. with an electric conductivity of $2.9 \times 10^{-1}$ S/cm $x = 0 020$, at a temperature of 150° C. with an electric conductivity of $1.6 \times 10^{-1}$ S/cm $x = 0.030$, at a temperature of 150° C. with an electric conductivity of $6.2 \times 10^{-2}$ S/cm $x = 0.040$, at a temperature of 150° C. with an electric conductivity of $3.3 \times 10^{-2}$ S/cm $x = 0.050$, at a temperature of 150° C. with an electric conductivity of $1.3 \times 10^{-2}$ S/cm $x = 0.000$, at a temperature of 200° C. with an electric conductivity of $21 \times 10^{-1}$ S/cm $x = 0.005$, at a temperature of 200° C. with an electric conductivity of $2.3 \times 10^{-1}$ S/cm $x = 0.010$, at a temperature of 200° C. with an electric conductivity of $3.3 \times 10^{-1}$ S/cm $x = 0.020$, at a temperature of 200° C. with an electric conductivity of $2.6 \times 10^{-1}$ S/cm $x = 0.030$, at a temperature of 200° C. with an electric conductivity of $1.2 \times 10^{-1}$ S/cm $x = 0.040$, at a temperature of 200° C. with an electric conductivity of $7.6 \times 10^{-2}$ S/cm $x = 0.050$, at a temperature of 200° C. with an electric conductivity of $3.2 \times 10^{-2}$ S/cm $x = 0.000$, at a temperature of 250° C. with an electric conductivity of $3.0 \times 10^{-1}$ S/cm $x = 0.005$, at a temperature of 250° C. with an electric conductivity of $3.0 \times 10^{-1}$ S/cm $x = 0.010$, at a temperature of 250° C. with an electric conductivity of $6.9 \times 10^{-1}$ S/cm $x = 0.020$, at a temperature of 250° C. with an electric conductivity of $41 \times 10^{-1}$ S/cm $x = 0.030$, at a temperature of 250° C. with an electric conductivity of $2.5 \times 10^{-1}$ S/cm $x = 0.040$, at a temperature of 250° C. with an electric conductivity of $1.7 \times 10^{-1}$ S/cm $x = 0.050$, at a temperature of 250° C. with an electric conductivity of $6.3 \times 10^{-2}$ S/cm At each temperature, higher density of the zirconium ion concentration allows the electric conductivity to rise, which is the highest when $x = 0.01$ to 0.02. According to the present invention, when $0 < x \leq 0.02$, the ionic conductivity is higher than that of the conventional fluoride ionic conductor, $PbSnF_4$ with the electric conductivity of $3.2 \times 10^{-2}$ S/cm.

Figure 2:
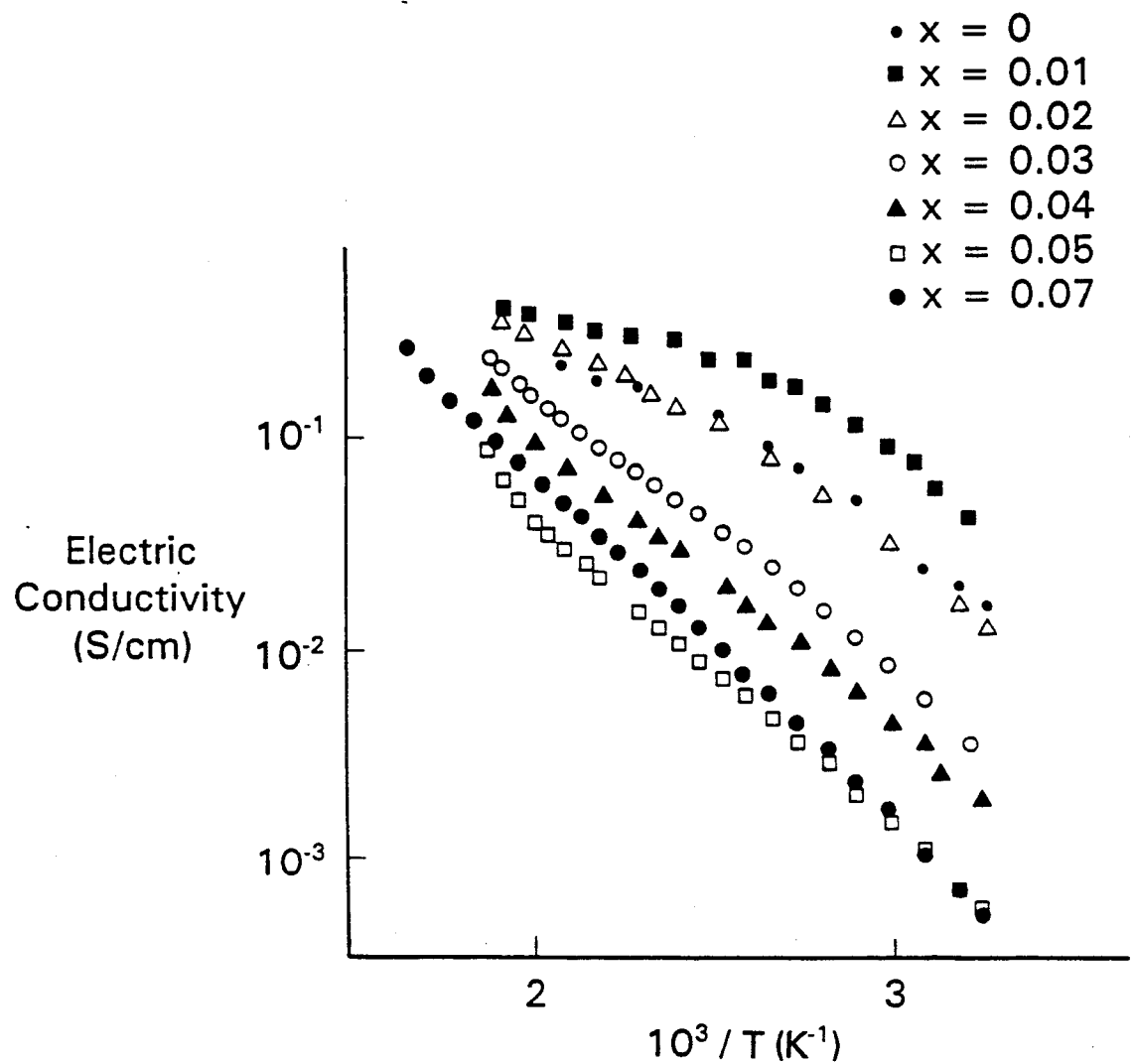
FIG. 2 is a diagram showing the relationship between the inverse of the absolute temperature and the electric conductivity of the fluoride ionic conductor (an Arrhenius plot) according to the first example of the present invention.
Figure 3:
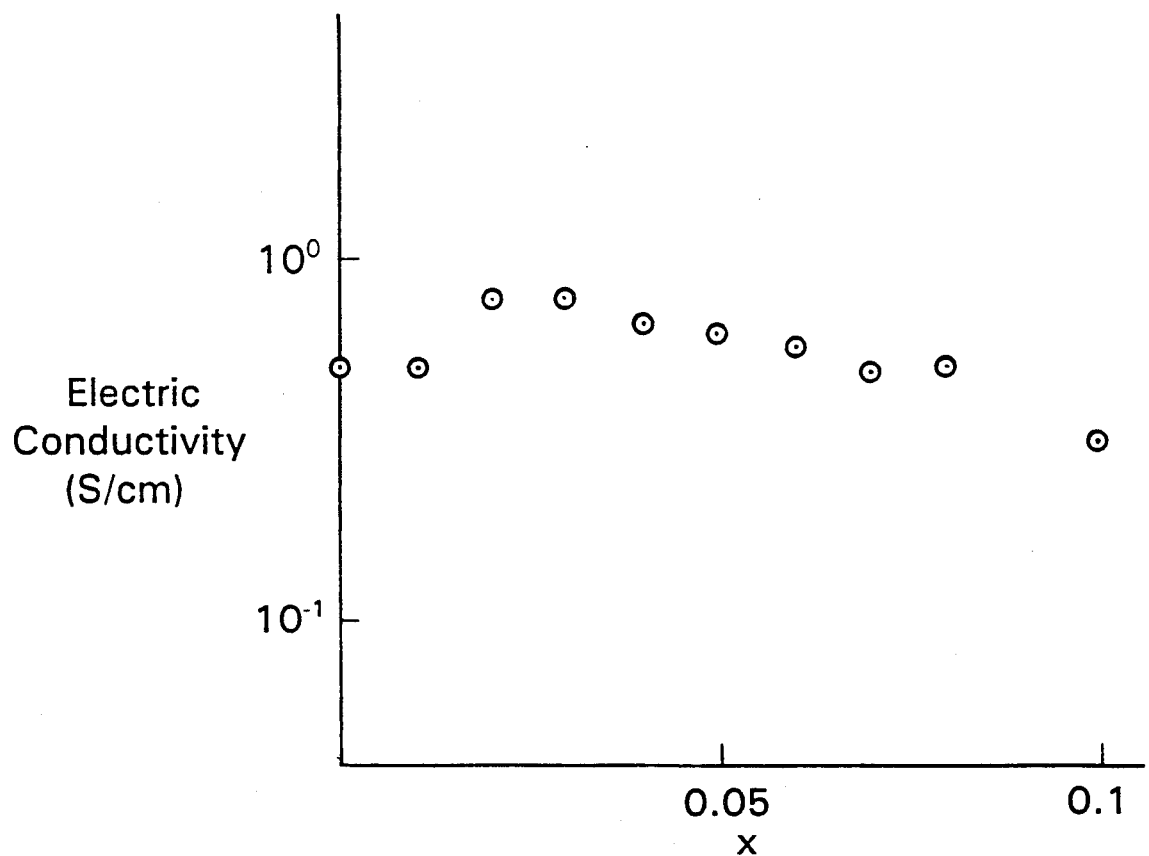
FIG. 3 is a diagram showing the relationship between the zirconium ion concentration of the fluoride ionic conductor and the electric conductivity at 400° C. according to the first example of the present invention.

FIG. 2 shows the relationship between the inverse of the absolute temperature and the electric conductivity (an Arrhenius plot) at each zirconium ion concentration (x). In the present invention, when $x \geq 0.03$, , the gradient of the line, that is, the activation energy, in the high temperature area, is larger than that of the conventional fluoride ionic conductor as shown in FIG. 2. By extrapolating the value, the electric conductivity at the temperature of 400° C. is estimated. (See also FIG. 3.)

When $x = 0.00$, the electric conductivity is $5.0 \times 10^{-1}$ S/cm.

When $x = 0.01$, the electric conductivity is $5.0 \times 10^{-1}$ S/cm.

When $x = 0.02$, the electric conductivity is $7.9 \times 10^{-1}$ S/cm.

When $x = 0.03$, the electric conductivity is $7.9 \times 10^{-1}$ S/cm.

When $x = 0.04$, the electric conductivity is $6.9 \times 10^{-1}$ S/cm.

When $x = 0.05$, the electric conductivity is $6.3 \times 10^{-1}$ S/cm.

When $x = 0.06$, the electric conductivity is $5.8 \times 10^{-1}$ S/cm.

When $x = 0.07$, the electric conductivity is $5.0 \times 10^{-1}$ S/cm.

When $x = 0.08$, the electric conductivity is $5.0 \times 10^{-1}$ S/cm.

When $x = 0.10$, the electric conductivity is $3.2 \times 10^{-1}$ S/cm.

In the first example of the present invention, when $x \leq 0.08$, the electric conductivity in the high temperature area is found to be improved compared with that of a conventional fluoride ionic conductor, $PbSnF_4$ with an electric conductivity of $5.0 \times 10^{-1}$ S/cm at 400° C.

As described above, the first example of the present invention can provide a fluoride ionic conductor with a higher ionic conductivity.

Example 2

The second example of the present invention will now be described in detail.

A fluoride ionic conductor with a composition of $Pb_{0.99}Sn_{1-y}Zr_{0.01+y}F_{4.02+2y}$ (wherein $0 < y \leq 0.15$), which is the composition of $Pb_{1-x}Sn_{1-y}Zr_{x+y}F_{4+2x+2y}$ (wherein $0.01 < x+y \leq 0.16$) when $x = 0.01$, is obtained as follows:

Lead fluoride ($PbF_2$), tin fluoride ($SnF_2$) and zirconium fluoride ($ZrF_4$) are used to make a sample. $PbF_2$, $SnF_2$ and $ZrF_4$ are weighed so as to make the molar ratio $0.99:1-y:0.01+y$, then crushed and mixed with an agate mortar (the average particle diameter: 50 μm). The crushed powder is molded into pellets with a diameter of 10 mm, a thickness of 3 mm and a powder density of 4.7 g/cm³ by a compression molding machine (temperature: room temperature, pressing time: 10 sec.).

The pellet is put in a reaction tube of nickel, the air in which has been exchanged for argon. Then hydrogen fluoride and argon as carrier gas are made to flow through the tube at a flow rate of 20 ml/min., and the tube is heated at 350° C. for six hours, thereby obtaining a sintered sample.

As a comparative example, a fluoride ionic conductor with a composition of $PbSnF_4$ is obtained. The same procedure as above is repeated to obtain a sintered sample except for using $PbF_2$ and $SnF_2$ with a 1:1 molar ratio.

In the thus obtained sintered sample of the fluoride ionic conductor gold is deposited as an electrode. The electric conductivity of the sample is measured in argon by the AC impedance measuring method (temperature: 60° C.).

The relationship between the zirconium ion concentration $(0.01+y)$ and the electric conductivity at each temperature is as follows:

$0.01 + y = 0.01$, at a temperature of 60° C. with an electric conductivity of $6.6 \times 10^{-2}$ S/cm
$0.01 + y = 0.02$, at a temperature of 60° C. with an electric conductivity of $3.0 \times 10^{-2}$ S/cm
$0.01 + y = 0.03$, at a temperature of 60° C. with an electric conductivity of $1.3 \times 10^{-2}$ S/cm
$0.01 + y = 0.04$, at a temperature of 60° C. with an electric conductivity of $3.0 \times 10^{-3}$ S/cm
$0.01 + y = 0.05$, at a temperature of 60° C. with an electric conductivity of $6.6 \times 10^{-4}$ S/cm At each temperature, higher density of the zirconium ion concentration allows the electric conductivity to rise, which is the highest when $0.01+y \approx 0.01$. According to the present invention, when $0.01+y \leq 0.02$, the ionic conductivity is higher than that of a conventional fluoride ionic conductor, $PbSnF_4$ with an electric conductivity of $3.2 \times 10^{-2}$ S/cm.

As described above, the second example of the present invention can provide a fluoride ionic conductor with a higher ionic conductivity.

Example 3

The third example of the present invention will now be described in detail.

A fluoride ionic conductor with a composition of $Pb_{1-x}Sn_{0.99}Zr_{x+0.01}F_{4.02+2x}$ (wherein $0 < x \leq 0.18$), which is the composition of $Pb_{1-x}Sn_{1-y}Zr_{x+y}F_{4+2x+2y}$ (wherein $0.01 < x+y \leq 0.19$) when $y=0.01$, is obtained as follows:

Lead fluoride ($PbF_2$), tin fluoride ($SnF_2$) and zirconium fluoride ($ZrF_4$) are used to make a sample. $PbF_2$, $SnF_2$ and $ZrF_4$ are weighed so as to make the molar ratio $1-x:0.99:x+0.01$, then crushed and mixed with an agate mortar (the average particle diameter: 50 μm). The crushed powder is molded into pellets with a diameter of 10 mm, a thickness of 3 mm and a powder density of 4.7 g/cm³ by a compression molding machine (temperature: room temperature, pressing time: 10 sec.).

The pellet is put in a reaction tube of nickel, the air in which has been exchanged for argon. Then hydrogen fluoride and argon as carrier gas are made to flow through the tube at a flow rate of 20 ml/min., and the tube is heated at 350° C. for six hours, thereby obtaining a sintered sample.

As a comparative example, a fluoride ionic conductor with a composition of $PbSnF_4$ is obtained.

The same procedure as above is repeated to obtain a sintered sample except for using $PbF_2$ and $SnF_2$ with a 1:1 molar ratio.

In the thus obtained sintered sample of the fluoride ionic conductor gold is deposited as an electrode. The electric conductivity of the sample is measured in argon by the AC impedance measuring method (temperature: 60° C.).

The relationship between the zirconium ion concentration $(x+0.01)$ and the electric conductivity at each temperature is as follows:

$x + 0.01 = 0.01$, at a temperature of 60° C. with an electric conductivity of $5.8 \times 10^{-2}$ S/cm
$x + 0.01 = 0.02$, at a temperature of 60° C. with an electric conductivity of $3.0 \times 10^{-2}$ S/cm
$x + 0.01 = 0.03$, at a temperature of 60° C. with an electric conductivity of $1.4 \times 10^{-2}$ S/cm
$x + 0.01 = 0.04$, at a temperature of 60° C. with an electric conductivity of $2.6 \times 10^{-3}$ S/cm
$x + 0.01 = 0.05$, at a temperature of 60° C. with an electric conductivity of $6.0 \times 10^{-4}$ S/cm At each temperature, higher density of the zirconium ion concentration allows the electric conductivity to rise, which is the highest when $x+0.01 \approx 0.01$. According to the present invention, when $x+0.01 \leq 0.02$, the ionic conductivity is higher than that of a conventional fluoride ionic conductor, $PbSnF_4$ with an electric conductivity of $3.2 \times 10^{-2}$ S/cm.

As described above, the third example of the present invention can provide a fluoride ionic conductor with a higher ionic conductivity.

Thus, the ionic conductor of the present invention is a crystal with a fluorite structure having an element of the fourth group of the periodic table as a cation and fluorine as an anion. When $ZrF_4$ is added, the zirconium ion exists in the crystal as a tetravalent cation. Therefore, the fluoride ions become excessive in the crystal lattice. These excessive fluoride ions contribute to the ionic conduction as interstitial ions. Thus the ionic conductor of the present invention has a high conductivity.

In the examples of the present invention, an ionic conductor including an element of the fourth group of the periodic table, fluorine and zirconium is described. Furthermore, an ionic conductor including an element of the second group of the periodic table, such as Ca, fluorine and zirconium can obtain the same effect.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. An ionic conductor used for a solid electrolyte comprising a solid fluorite crystal structure containing the elements fluorine, zirconium, tin and lead.

2. An ionic conductor according to claim 1, being $Pb_{1-x}Sn_{1-y}Zr_{x+y}F_{4+2x+2y}$ wherein $0 < x+y \leq 0.16$.

3. An ionic conductor according to claim 1, being $Pb_{1-x}Sn_{1-y}Zr_{x+y}F_{4+2x+2y}$ wherein $0 < x+y \leq 0.02$.

4. An ionic conductor according to claim 1, the fluorine being in the form of an anion, and the zirconium and the tin and the lead being in the form of a cation.

5. An ionic conductor used for a solid electrolyte comprising a compound containing the elements fluorine, zirconium, tin and lead.

* * * * *

UNITED STATES PATENT AND TRADEMARK OFFICE
CERTIFICATE OF CORRECTION

PATENT NO. : 5,320,917
DATED : June 14, 1994
INVENTOR(S) : Kazunori Takada, Shigeo Kondo It is certified that error appears in the above-indentified patent and that said Letters Patent is hereby corrected as shown below:

Col. 3, line 40, replace "21" with --2.1--.

Col. 3, line 60, replace "41" with --4.1--.

In Figure 1 of the drawings and the figure which appears on title page, "log ($\delta$/Scm$^{-1}$)" S/B --log ($\sigma$/Scm$^{-1}$)-- on the vertical axis.

Signed and Sealed this

Third Day of January, 1995

Attest:

BRUCE LEHMAN

Attesting Officer

Commissioner of Patents and Trademarks